United States Patent [19]
Kodama et al.

[11] Patent Number: 5,844,801
[45] Date of Patent: Dec. 1, 1998

[54] METHOD OF INSPECTING AND MANUFACTURING VEHICLE BODY

[75] Inventors: Akira Kodama; Yasuhiko Kitano; Hiroya Miyaoka; Hisato Morita; Takashi Uehara; Hideaki Maruyama; Tadatoshi Tsuji; Nobuhiro Nagao; Yoshikazu Kaizu, all of Sayama, Japan

[73] Assignee: Honda Giken Kogyo Kabushiki Kaisha, Tokyo, Japan

[21] Appl. No.: 530,893

[22] Filed: Sep. 20, 1995

[30] Foreign Application Priority Data

| Dec. 8, 1994 | [JP] | Japan | 6-304690 |
| Dec. 12, 1994 | [JP] | Japan | 6-307933 |
| Dec. 26, 1994 | [JP] | Japan | 6-322724 |
| Mar. 16, 1995 | [JP] | Japan | 7-057083 |

[51] Int. Cl.⁶ .................................................. G06F 17/60
[52] U.S. Cl. .................. 364/468.17; 364/552; 382/141
[58] Field of Search ................. 364/468.17, 468.16, 364/551.01, 552, 554, 560–564, 566, 571.05; 356/445–448; 382/108, 141, 152

[56] References Cited

U.S. PATENT DOCUMENTS 4,920,385  4/1990  Clarke et al. .

FOREIGN PATENT DOCUMENTS

| 0405806 | 1/1991 | European Pat. Off. . |
| 48-7986 | 3/1973 | Japan . |
| 1-132908 | 5/1987 | Japan . |
| 62-110138 | 5/1987 | Japan . |
| 3-175000 | 7/1991 | Japan . |
| 5-322534 | 7/1993 | Japan . |
| 5-322535 | 7/1993 | Japan . |
| 6-1249 | 5/1994 | Japan . |
| 6-148082 | 5/1994 | Japan . |
| WO 85/03776 | 8/1985 | WIPO . |
| WO8605588A1 | 9/1986 | WIPO . |

*Primary Examiner*—James P. Trammell
*Attorney, Agent, or Firm*—Birch, Stewart, Kolasch & Birch, LLP

[57] ABSTRACT

After outer panels have been assembled on a vehicle frame, they are coated with an aqueous lustering agent P, and then irradiated with a light beam L. Light reflected by the outer panels is processed to produce a degree and range of distortion thereof. Based on the produced degree and range of distortion, it is determined whether the outer panels suffer a surface distortion or not. The determined result is displayed on a display monitor. According to the displayed image, the outer panels are repaired and thereafter coated with a paint.

22 Claims, 20 Drawing Sheets

METHOD OF INSPECTING AND MANUFACTURING VEHICLE BODY

BACKGROUND OF THE INVENTION

1. Field of the Invention

The present invention relates to a method of assembling outer panels on a vehicle frame thereby to manufacture a vehicle body, and thereafter inspecting the surface profile of the vehicle body including the outer panels and, if necessary, correcting the vehicle body, before the vehicle body is coated.

2. Description of the Related Art

Outer panels for vehicle bodies that have been pressed or otherwise produced may suffer surface defects or distortions such as surface irregularities, dents, bumps, strains, or the like because of inadvertent handling. If a produced outer panel has such a surface distortion, it tends to undergo a serious problem in a subsequent process. For example, when an outer panel with a surface distortion is coated, the surface distortion causes a coating defect, which lowers the commercial value of the coated outer panel.

According to one conventional process disclosed in Japanese laid-open patent publication No. 3-175000, for example, outer panels including door panels, roof panels, engine hood panels, etc. for vehicle bodies are individually inspected for their surface profiles. Those outer panels that have been accepted are assembled into vehicle bodies, which are then coated.

A process of manufacturing vehicle bodies is composed of many steps that have to be carried out until outer panels are assembled on a vehicle frame. For example, an outer panel produced by pressing sheet metal is hemmed to shape, and then necessary parts are mounted on the outer panel at respective positions thereon, after which the outer panel is delivered to a coating station. In each of the above steps, the outer panel may be scratched, damaged, or deformed due to poor handling. Once a defective outer panel is coated, the coated outer panel will be a poor product, whose defective area can no longer be corrected. As a result, such a manufacturing process suffers a poor yield.

The above process of inspecting outer panels for their surface profiles has heretofore been carried out by the operator in an organoleptic test. The organoleptic test requires a high level of skill on the part of the operator and necessarily results in a subjective decision as to the determination of whether a tested outer panel is defective or not.

In an effort to avoid the above drawbacks of the organoleptic inspection process, there have been proposed automatic processes or apparatus for automatically inspecting products as disclosed in Japanese patent publication No. 6-1249 and Japanese laid-open patent publication No. 3-175000. According to the prior art revealed in Japanese patent publication No. 6-1249, the surface of an outer panel which is to be inspected is irradiated with illuminating light, and the reflected light is applied again to the surface of the outer panel by a light reversing element. The light which is reflected once more by the surface of the outer panel forms an image, whose lights and shades are used to detect any surface irregularities of the outer panel. According to the arrangement shown in Japanese laid-open patent publication No. 3-175000, the entire surface of an outer panel is illuminated with uniform illuminance, and an image of the illuminated surface is read, whereupon any surface irregularities of the outer panel are detected based on lights and shades of the image.

While the above conventional processes are capable of detecting surface irregularities of the outer panel, they fail to detect how large those detected surface irregularities are. Since these processes cannot produce enough information as to whether the detected surface irregularities should be interpreted to judge the outer panel defective or not, the operator will eventually be called in to visually confirm the outer panel for deciding on the outer panel.

Japanese laid-open patent publication No. 62-110138 shows a known inspecting process for classifying a distortion on an inspected surface into a rank depending on the size of the distortion and displaying the rank, allowing the operator to recognize how large the distortion is.

However, there are instances in which a surface distortion on a tested product does not need to be recognized as a defect depending on the irregularity of the surface distortion or the magnitude of the curvature thereof, in view of the surface profile of a reference product. As a consequence, surface distortions cannot be judged only from their size.

Japanese laid-open patent publication No. 1-132908 discloses a prior inspecting process in which uniform light is applied to a tested product in a direction normal to a weld line on the product, and the continuity of the weld line is detected on the basis of the image of the weld line which is read. The disclosed inspecting process, however, cannot easily detect large undulations of the weld line, and is incapable of detect concave distortions.

Prior attempts to eliminate the above deficiencies of the prior art are proposed in Japanese laid-open patent publications Nos. 5-322534 and 5-322535. According to these proposals, light reflected from an object which is irradiated with a linear laser beam is captured by a camera, and an image produced by the camera is compared with CAD data which is reference profile data for the object. Positive and negative values of errors of the image with respect to the CAD data are displaced in different colors as a graphic image.

The above prior process is capable of confirming whether the image has an error or not, but fails to determine whether a detected error is acceptable or not.

According to another inspecting process disclosed in Japanese laid-open patent publication No. 6-148082, the surface of a panel which is to be inspected is irradiated with illuminating light from a point source, and the reflected light is applied again to the surface of the panel by a light reversing screen. An image formed by the light which is reflected once more by the surface of the panel is captured by a camera, and its lights and shades are processed to determine a range and degree of distortion. The determined range and degree of distortion is compared with predetermined values to determine whether the detected distortions are acceptable or not.

In the above inspecting process, the lights and shades of the image are emphasized or sharpened in edge and then converted into binary values to extract distortions for determining a distortion range. Therefore, those surface distortions which form an image of lesser lights and shades may not be extracted due to rounding errors produced upon conversion into binary values. Even if those surface distortions are extracted, a surface distortion range may not be determined with high accuracy.

With respect to images of lights and shades produced from surface distortions, the degree or depth of relatively small distortions is commensurate with the density of the image, and hence is close to actually measured values. If the degree or depth of surface distortions is relatively large, then it is no longer commensurate with the density of the image, with the result that degree or depth of surface distortions cannot be determined highly accurately from the density of the image.

When the surface of a product is scanned with a light beam and the reflected light is processed to detect any surface distortions of the product, if the surface of the product is not lustrous or has a very low reflectance, then a surface image suitable for subsequent processing cannot be formed, and the accuracy of detecting distortions is lowered.

One conventional process proposed to solve the above problems prevents light from suffering diffuse reflection by coating the surface of a product with an oily liquid composed of lustrous oil, as disclosed in Japanese laid-open patent publication No. 3-175000. A highly volatile liquid may be coated, instead of the oily liquid, on the product surface, so that the liquid will not remain on the product surface upon subsequent processing, as disclosed in Japanese patent publication No. 48-7986.

It is preferable to employ an electrostatic coating process, for example, to form a uniform lustrous surface with an oily liquid composed of lustrous oil. Since, however, the oily liquid is electrically conductive, an electrostatic coating apparatus that is used has to be electrically insulated, thus making the entire process highly expensive. While a highly volatile liquid, such as alcohol, trichloroethylene, or the like, is electrically nonconductive, requiring no electrical insulation on the electrostatic coating apparatus, the highly volatile liquid needs a considerable amount of care in handling as it is flammable and toxic.

SUMMARY OF THE INVENTION

It is a general object of the present invention to provide a method of inspecting and manufacturing a vehicle body by inspecting and correcting the surface of the vehicle body to increase the yield of coated vehicle bodies.

A main object of the present invention is to provide a method of manufacturing a vehicle body, which is capable of detecting a defective location on the surface of a vehicle body at an optimum time.

Another object of the present invention is to provide a method of manufacturing a vehicle body, which can be carried out easily and allows suitable surface treatment to be effected inexpensively.

Still another object of the present invention is to provide a method of inspecting a vehicle body for automatically determining whether the surface of a product is acceptable or not based on suitable standards.

Yet still another object of the present invention is to provide a method of inspecting a vehicle body, which is capable of calculating a range and degree of distortion, for use as reference data for determining surface distortions, highly accurately from luminance information of the surface of a product.

The above and other objects, features, and advantages of the present invention will become apparent from the following description when taken in conjunction with the accompanying drawings in which preferred embodiments of the present invention are shown by way of example.

DETAILED DESCRIPTION OF THE PREFERRED EMBODIMENTS

Figure 1:
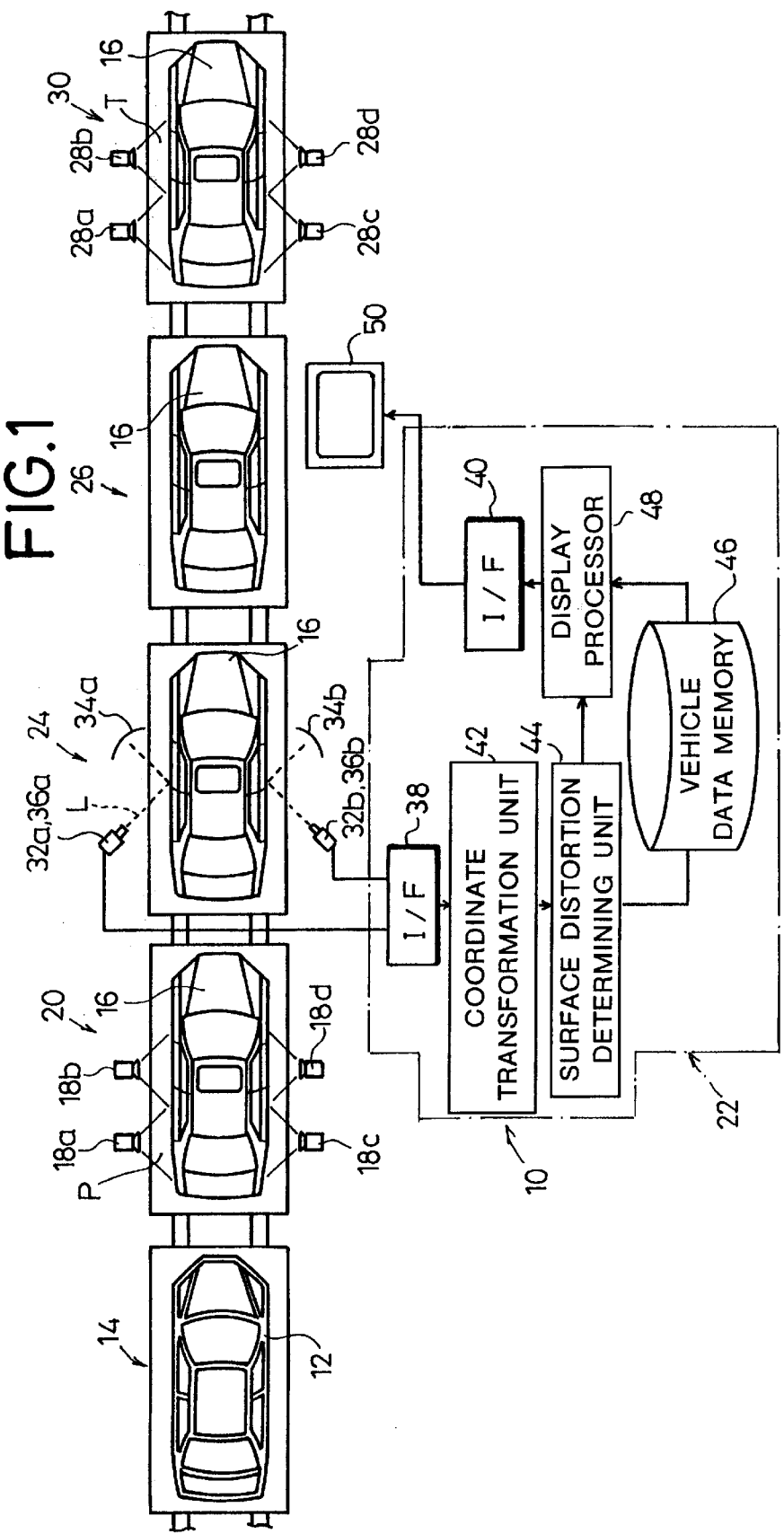
FIG. 1 is a schematic plan view, partly in block form, a vehicle body production system to which a method of manufacturing a vehicle body according to the present invention is applied.

FIG. 1 schematically shows, partly in block form, a vehicle body production system to which a method of manufacturing a vehicle body according to the present invention is applied.

The vehicle body production system, generally designated by the reference numeral 10, comprises an assembling station 14 in which outer panels including door panels, a roof panel, an engine hood panel, and a trunk lid panel are assembled on a vehicle frame 12, producing a vehicle body 16, a lustering station 20 for coating a lustering agent P on the vehicle body 16 with two pairs of spray guns 18a~18d, one pair on each side of the lustering station 20, a surface inspecting station 24 for inspecting the surface of the vehicle body 16 with a surface inspecting apparatus 22, a repairing station 26 for repairing the vehicle body 16 based on the results of a surface inspecting process carried out in the surface inspecting station 24, and a coating station 30 for coating a paint solution T on the surface of the vehicle body 16 with spray guns 28a~28d.

The surface inspecting apparatus 22 has a pair of light sources 32a, 32b disposed one on each side of the surface inspecting station 24 for applying a light beam L to the vehicle body 16, a pair of condensers 34a, 34b for concentrating light reflected from the vehicle body 16 irradiated with the light beam L, and a pair of cameras 36a, 36b comprising respective CCDs or the like for detecting light reflected from the condensers 34a, 34b to obtain an image of the surface of the vehicle body 16. The surface inspecting apparatus 22 also has a pair of interfaces 38, 40, a coordinate transformation unit 42 for transforming the coordinates of the surface image data produced by the cameras 36a, 36b to generate surface profile data, a surface distortion determining unit 44 for comparing the surface profile data with reference vehicle body data to identify defective areas of the vehicle body 16 where surface distortions are present, a vehicle data memory 46 for storing the reference vehicle body data, a display processor 48 for processing defective area data to display the defective areas according to the reference vehicle body data, and a display monitor 50 positioned at the repairing station 26 for displaying the vehicle body profile and the defective areas.

Figure 2:
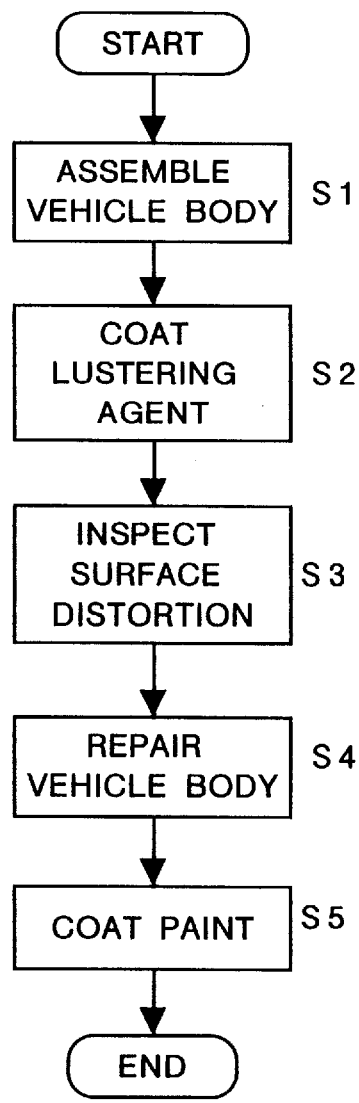
FIG. 2 is a flowchart of an operation sequence of the vehicle body production system shown in FIG. 1.

An operation sequence of the vehicle body production system 10 will be described in detail with reference to FIG. 2.

First, outer panels including door panels, a roof panel, an engine hood panel, and a trunk lid panel are formed by a press or the like, and then hemmed, after which necessary parts are mounted on the outer panels. The outer panels are then assembled on the vehicle frame 12 transferred from an upstream area in the assembling station 14, thereby producing the vehicle body 16 in a step S1.

Then, the vehicle body 16 is fed to the lustering station 20 in which a lustering agent P is coated on the surface of the vehicle body 16 under pneumatic pressure by the two pairs of spray guns 18a~18d in a step S2. The lustering agent P is an aqueous lustering agent which comprises an aqueous solution of 15~20% of an anionic surface-active agent such as of lauric acid, polyethylene glycol, or the like, which is mixed with a rust-resistant agent and a leveling agent. Alternatively, the lustering agent P may comprise an emulsion of an cationic or aqueous surface-active agent and a petroleum solvent.

Figure 3:
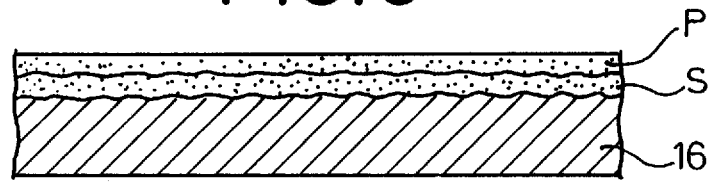
FIG. 3 is an enlarged fragmentary cross-sectional view showing a thin film of lustering agent that is formed on the surface of a product through an intervening film of oil.

As shown in FIG. 3, a film of forming oil S such as liquid paraffin which was applied when the outer panels were pressed to shape may possibly remain on the vehicle body 16. If such a film of forming oil S remains coated on the surface of the vehicle body 16, then the lustering agent P is coated on the remaining film of forming oil S.

Figure 4A:
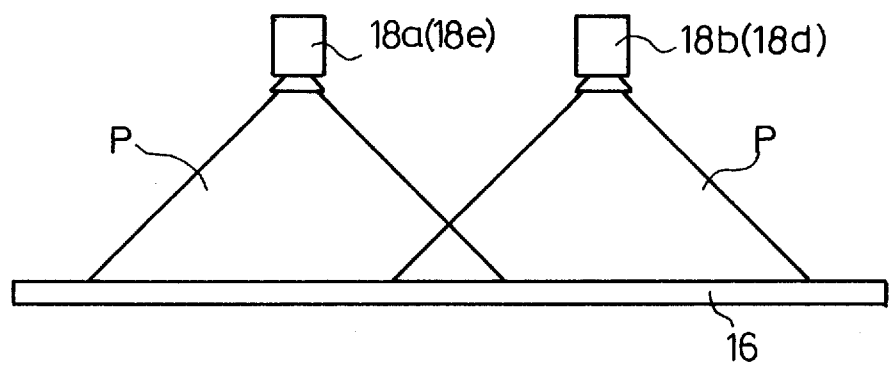
FIG. 4A is a view showing an arrangement of spray guns in a lustering station in the vehicle body production system shown in FIG. 1.
Figure 4B:
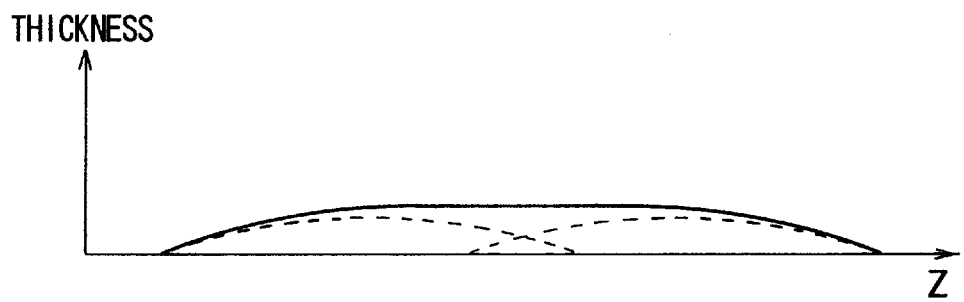
FIG. 4B is a diagram illustrative of the thickness of the thin film of lustering agent on the surface of the product.

The liquid paraffin is a nonpolar lipophilic solvent, whereas the anionic surface-active agent of the lustering agent P is a polar hydrophilic solvent. Since the anionic surface-active agent is diluted by water, its surface tension is small, and its wettability is large with respect to the vehicle body 16. Therefore, the lustering agent P is dispersed in the film of forming oil S due to its emulsifying action, and uniformly spread, forming a thin lustrous film on the vehicle body 16. In this embodiment, the two spray guns 18a (18c), 18b (18d) on each side of the lustering station 20 are used to coat the lustering agent P in respective patterns which overlap each other in an intermediate area between the patterns as shown in FIG. 4A. Although the coated film of lustering agent P produced by each of the spray guns 18a (18c), 18b (18d) has a thickness indicated by the dotted lines in FIG. 4B, the combined film has a substantially uniform thickness indicated by the solid line in FIG. 4B because the lustering agent P is coated in overlapping patterns as described above. As a result, the thin lustrous film coated on the vehicle body 16 has a substantially uniform thickness.

When the lustering agent P is coated on the vehicle body 16, the lustering agent P is sprayed under pneumatic pressure from the spray guns 18a~18d. Since the surface tension of the lustering agent P is small, the lustering agent P can be coated into a thin lustrous film of substantially uniform thickness even if it is not coated by an electrostatic coating process. Therefore, the coating apparatus used in the lustering station 20 may be relatively inexpensive. Furthermore, the aqueous lustering agent P is much more easy to handle than an oily or volatile lustering agent.

In forming an appropriate thin lustrous film of the forming oil S and the lustering agent P, it is important to control the concentration of the lustering agent P in order to adjust the surface tension thereof. If the concentration of the water-diluted surface-active agent of the lustering agent P were too low, it would be difficult to smooth the surface of the vehicle body 16. On the other hand, if the concentration of the water-diluted surface-active agent of the lustering agent P were too high, the viscosity of the lustering agent P would be so high that bubbles would be formed when the lustering agent P is coated, making it difficult to wash away the lustering agent P after the vehicle body 16 is inspected for surface distortions. The concentration of the water-diluted surface-active agent of the lustering agent P is preferably in the range of 15 to 20%.

The vehicle body 16 on which the thin lustrous film of substantially uniform thickness has been formed by the lustering agent P is then delivered to the surface inspecting station 24 in which the vehicle body 16 is inspected for surface distortions by the surface inspecting apparatus 22 in a step S3. Specifically, a light beam L emitted from the light sources 32a, 32b are reflected by the surface of the vehicle body 16 and concentrated by the condensers 34a, 34b, which reflect the concentrated light to the cameras 36a, 36b. The cameras 36a, 36b produce an image of the surface of the vehicle body 16 based on the reflected light, and the image is supplied as surface image data through the interface 38 to the coordinate transformation unit 42. The coordinate transformation unit 42 transforms the coordinates of the surface image data thereby to generate surface profile data of the vehicle body 16.

Figure 5:
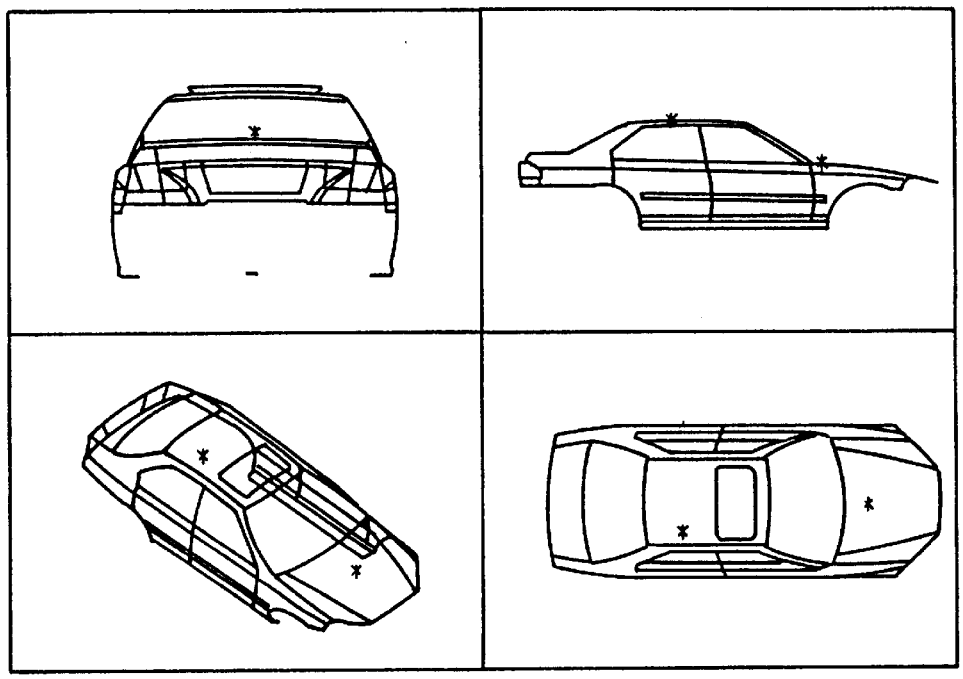
FIG. 5 is a view showing determined surface distortions displayed on a display monitor at a repairing station in the vehicle body production system shown in FIG. 1.

The surface distortion determining unit 44 compares the surface profile data with reference vehicle body data stored in the vehicle data memory 46, then compares the degree or depth of each of distortions produced by the comparison, with a predetermined threshold value, and identifies each of areas whose degree of distortion exceeds the predetermined threshold value as a defective area. Because the outer panels have been assembled on the vehicle frame 12 and necessary parts have been mounted thereon, each defective area may have been produced not only when the outer panels were pressed, but also when the vehicle body 16 was processed in the assembling station 14 and the lustering station 20. Positional data relative to each defective area is combined with the reference vehicle body data in the display processor 48, and transferred through the interface 40 to the display monitor 50 where it is displayed. As shown in FIG. 5, the display monitor 50 disposed at the repairing station 26 displays images of the vehicle body 16 and defective areas (indicated by an asterisk) thereon.

After the surface inspection, the vehicle body 16 is fed to the repairing station 26 and repaired based on the defective areas displayed on the display monitor 50 in a step S4.

The repaired vehicle body 16 is then delivered to the coating station 30 in which a paint is coated on the surface of the vehicle body 16 by the spray guns 28a~28d in a step S5. Since the defective areas have been removed from the vehicle body 16 in the repairing station 26 immediately upstream of the coating station 30, the coated vehicle body 16 will be supplied as a defect-free product to a next processing stage.

A surface inspecting method according to another embodiment of the present invention, which may be carried out in the surface inspecting station 24, will be described below.

Figure 6:
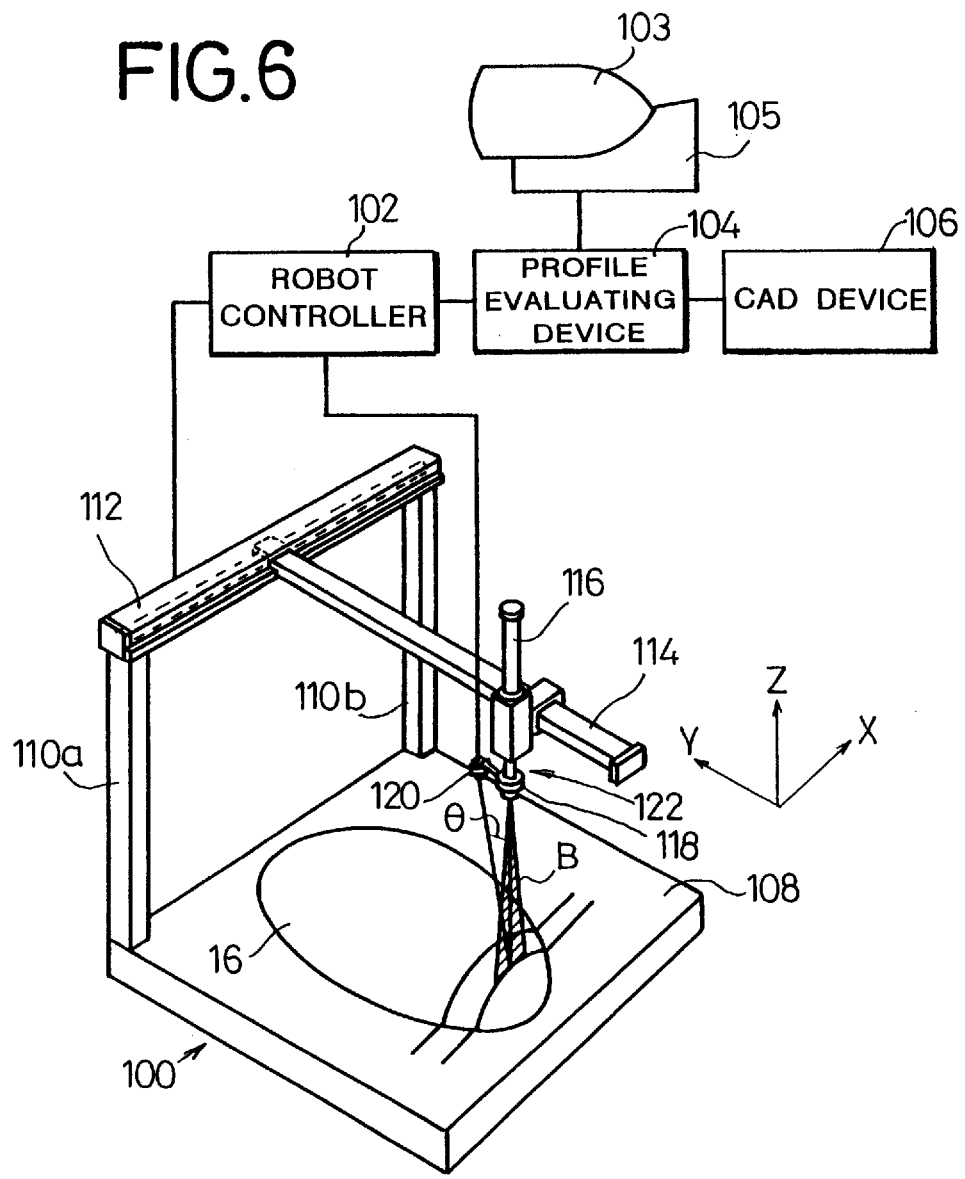
FIG. 6 is a perspective view, partly in block form, of another surface inspecting apparatus.

FIG. 6 shows, partly in block form, of another surface inspecting apparatus. As shown in FIG. 6, the surface inspecting apparatus comprises a profile measuring robot 100 for measuring the surface profile of the vehicle body 16, a robot controller 102 for controlling the profile measuring robot 100, a profile evaluating device 104 for evaluating measured surface profile data of the vehicle body 16 which has been produced by the profile measuring robot 100, the profile evaluating device 104 being associated with a CRT display 103 and a keyboard 105, and a CAD device 106 for supplying reference surface profile data composed of design data of the vehicle body 16 to the profile evaluating device 104.

Figure 7:
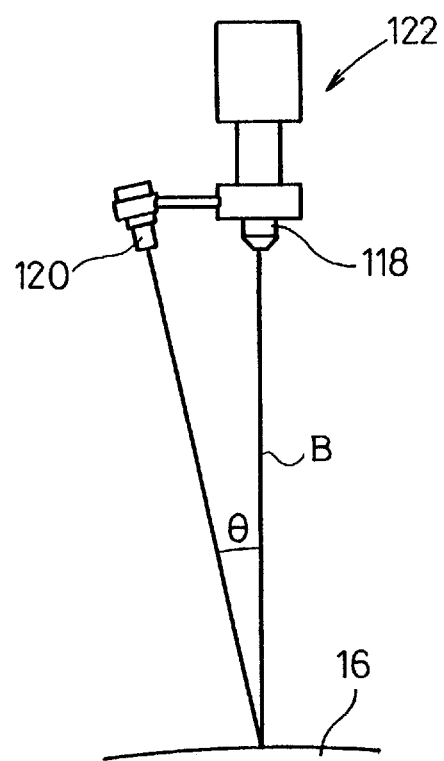
FIG. 7 is a schematic view of a measuring unit of the surface inspecting apparatus shown in FIG. 6.

The profile measuring robot 100 has a table 108 for placing the vehicle body 16 thereon, a pair of spaced support columns 110a, 110b mounted vertically on one end of the table 108, an X-axis guide rail 112 mounted on and extending between the upper ends of the support columns 110a, 110b, a Y-axis guide rail 114 movably supported at one end thereof on the X-axis guide rail 112 in overhanging relation to the table 108, and a Z-axis guide rod 116 movably mounted on the Y-axis guide rail 114. The Y-axis guide rail 114 is movable in the direction of an X-axis parallel to the X-axis guide rail 112, and the Z-axis guide rod 116 is movable in the direction of a Y-axis parallel to the Y-axis guide rail 114 and also in the direction of a Z-axis which extends vertically perpendicularly to the X- and Y-axes. The Z-axis guide rod 116 supports on a lower end thereof a measuring unit 122 which comprises a head 118 for applying a laser beam B, which spreads in a vertical plane in the direction of an X-axis parallel to the X-axis guide rail 112, to the vehicle body 16 placed on the table 108, and a camera 120 for detecting the laser beam B reflected by the vehicle body 16. The measuring unit 122 is thus movable three-dimensionally in the directions of the X-, Y-, Z-axes. As shown in FIG. 7, the camera 120 is inclined at an angle θ (>0) to the optical axis of the laser beam B which is emitted downwardly from the measuring head 118.

Figure 8:
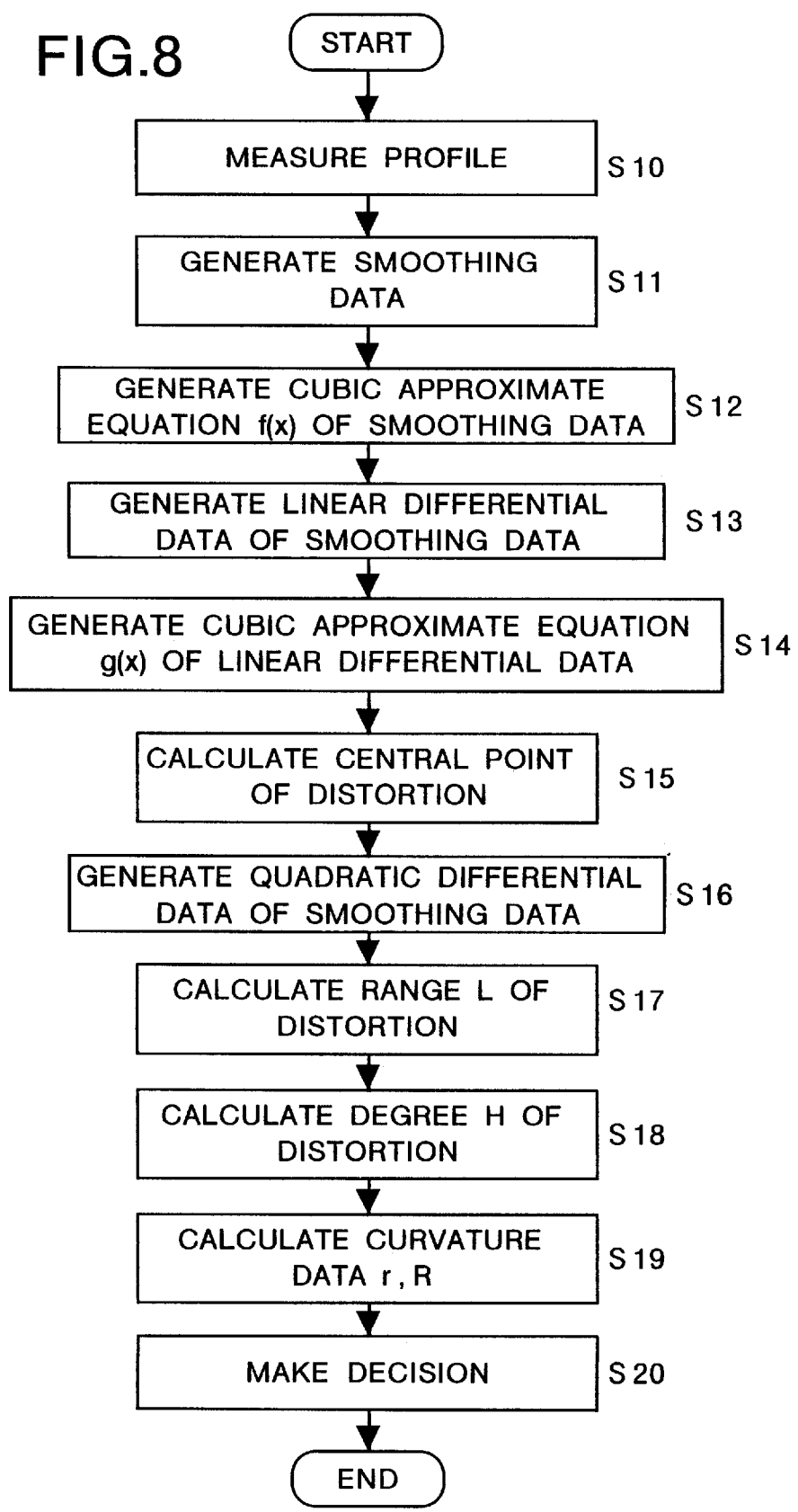
FIG. 8 is a flowchart of an operation sequence of a surface inspecting method according to another embodiment of the present invention.

An operation sequence of the surface inspecting method according to the other embodiment of the present invention, which is carried out by the surface inspecting apparatus shown in FIGS. 6 and 7, will be described below with reference to FIG. 8.

Figure 9:
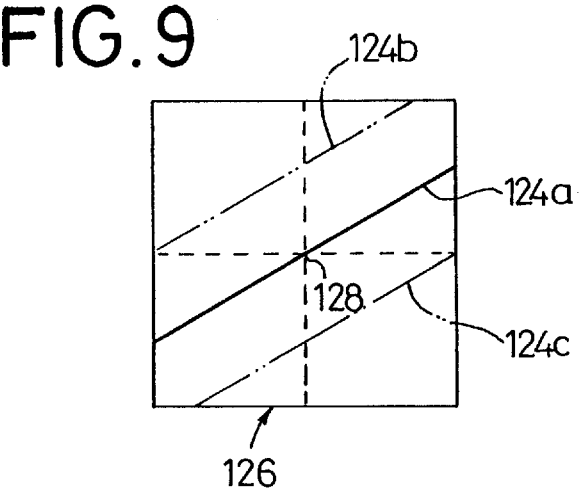
FIG. 9 is a diagram illustrative of the principle of profile measurement effected by a profile measuring robot of the surface inspecting apparatus shown in FIG. 6.

First, the robot controller 102 controls the Y-axis guide rail 114 to move a distance of ΔX along the X-axis guide rail 112 for thereby scanning the vehicle body 16 in the direction of the X-axis with the laser beam B emitted from the measuring head 118. The laser beam B reflected by the surface of the vehicle body 16 is then detected by the camera 120. Since the camera 120 reads the laser beam B which spreads in the vertical plane in the direction of the X-axis at the angle θ to the vertical plane, the image of the laser beam B which is produced by the camera 120 is one of linear images 124a, 124b, 124c indicated by the solid- and two-dot-and-dash lines in FIG. 9. The robot controller 102 actuates the Z-axis guide rod 116 to displace the measuring unit 122 a distance of ΔZ in the direction of the Z-axis in order to cause the one of the linear images 124a, 124b, 124c to pass through the center 128 of an imaged area 126 of the camera 120. When one scanning cycle in the direction of the X-axis is completed, the robot controller 102 moves the measuring unit 122 a distance of ΔY along the Y-axis guide rail 114, and thereafter moves the measuring unit 122 to scan the vehicle body 16 again in the direction of the X-axis with the laser beam B emitted from the measuring head 118. The above displacements ΔX, ΔY, ΔZ of the measuring unit 122 are supplied to the profile evaluating device 104, which generates measured surface profile data $(x_i, y_i, z_i)$ (i=1, ..., n, n: measuring point number) of the vehicle body 16 in a step S10.

Cross-sectional profile data $z_i$ of the measured surface profile data $(x_i, y_i, z_i)$ is averaged over every nine points in the direction of the X-axis as indicated by the following equation (1), thereby determining smoothed data $s_i$ in a step S11. This averaging process can provide data free of measuring noise.

$$s_i = \sum_{j=i-4}^{i+4} Z_j/9 \tag{1}$$

Figure 10:
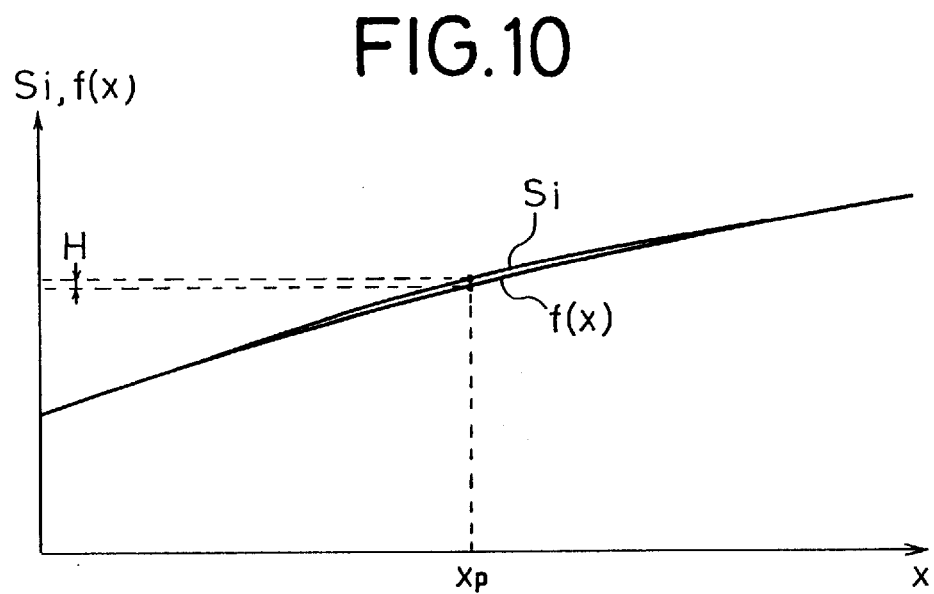
FIG. 10 is a diagram illustrative of smoothed data obtained from measured surface profile data and an approximate equation of such smoothed data.

Then, a cubic approximate equation f(x) is determined from the smoothed data $s_i$ using the method of least squares in a step S12, where "x" is a continuous variable of $x_i$. Because the approximate equation f(x) represents a smoothed form (smoothed measured surface profile data) of the smoothed data $s_i$, it is regarded as indicating a cross section of the surface of the vehicle body 16 in which no distortions are visually recognized. FIG. 10 shows the smoothed data $s_i$ and the approximate equation f(x) thus determined as they overlap each other. The difference between the smoothed data $s_i$ and the approximate equation f(x) represents a distortion that can be visually recognized.

Thereafter, the smoothed data $s_i$ is differentiated according to the equation (2) given below, for example, determining linear differential data $s'_i$ in a step S13, and a cubic approximate equation g(x) is determined from the linear differential data $s'_i$ using the method of least squares in a step S14.

$$s'_i = \frac{z_{i+3} - z_{i-3}}{x_{i+3} - x_{i-3}} \quad (2)$$

Figure 11:
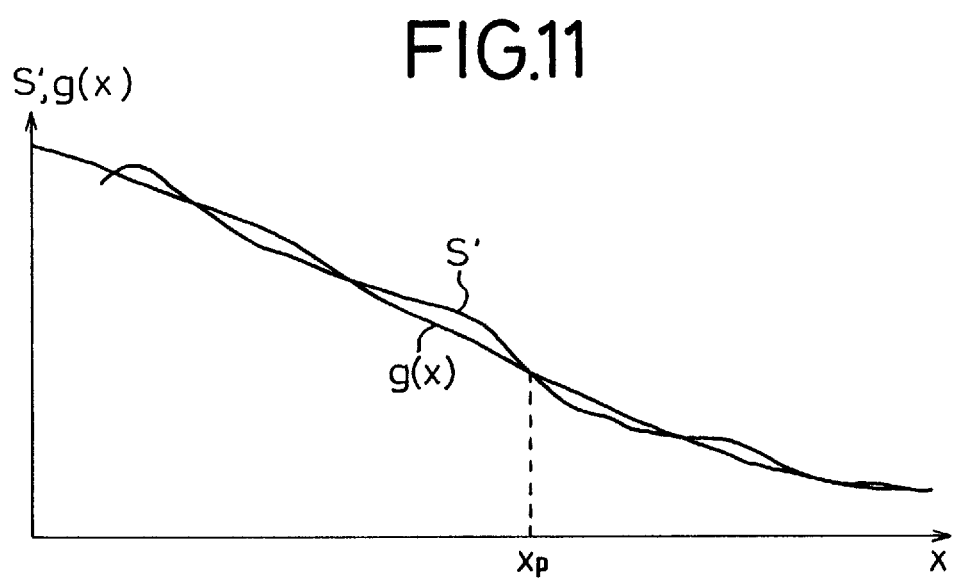
FIG. 11 is a diagram illustrative of linear differential data of smoothed data and an approximate equation of such linear differential data.

The linear differential data $s'_i$ represents a gradient of the cross section of the surface of the vehicle body 16 which is indicated by the smoothed data $s_i$, and the cubic approximate equation g(x) represents a smoothed form (smoothed linear differential data) of the linear differential data $s'_i$. Therefore, the cubic approximate equation g(x) is regarded as indicating a gradient of the cross section of the surface of the vehicle body 16 in which no distortions are visually recognized. FIG. 11 shows the linear differential data $s'_i$ and the approximate equation g(x) thus determined as they overlap each other. Now, a central point $x_P$ of the distortion shown in FIG. 10 is determined as a point where the linear differential data $s'_i$ changes from a value greater than the approximate equation g(x) to a value smaller than the approximate equation g(x), or from a value smaller than the approximate equation g(x) to a value greater than the approximate equation g(x) in a step S15, because the largest distortion can be regarded as occurring at the point.

Then, the linear differential data $s'_i$ is differentiated according to the equation (3) given below, for example, determining quadratic differential data $s''_i$ in a step S16.

$$s''_i = \frac{s'_{i+3} - s'_{i-3}}{x_{i+3} - x_{i-3}} \quad (3)$$

Figure 12:
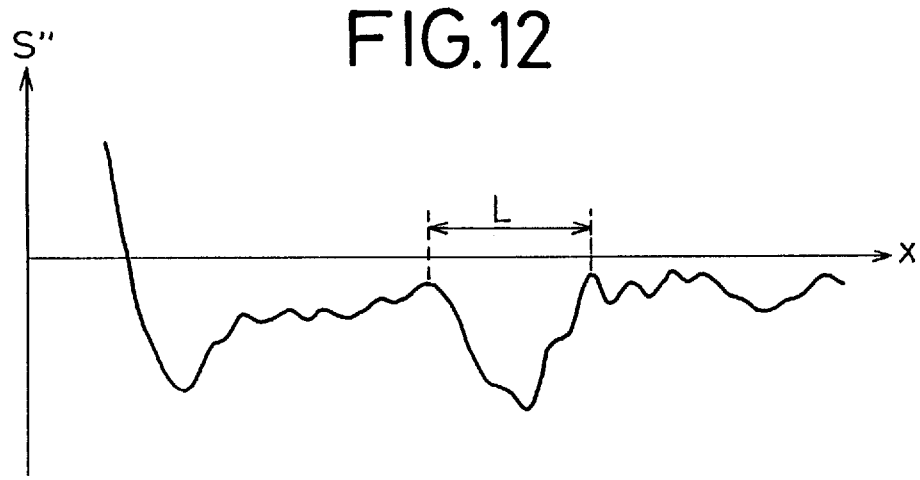
FIG. 12 is a diagram illustrative of quadratic differential data of smoothed data.

The quadratic differential data $s''_i$ represents a change of the gradient of the cross section of the surface of the vehicle body 16 which is indicated by the smoothed data $s_i$. A range in which the change of the gradient is large is determined as a range L of distortion in a step S17. FIG. 12 shows the quadratic differential data $s''_i$ thus determined. The range L of distortion can be automatically determined by extracting a maximum value of the quadratic differential data $s''_i$ which is greater or smaller than a predetermined value.

Then, a degree or depth H of distortion at the central point $x_P$ determined in the step S15 is determined as:

$$H = s(x_P) - f(x_P) \quad (4)$$

in a step S18 (see FIG. 10).

Then, curvature data r of the cross section of the surface of the vehicle body 16 which is determined from the smoothed data $s_i$ at the central point $x_P$, and curvature data R of the cross section of the surface of the vehicle body 16 which is determined from the approximate equation f(x) at the central point $x_P$ are determined from the radius of an arc that passes through the central point $x_P$ and two points one on each side thereof in a step S19.

Figure 13:
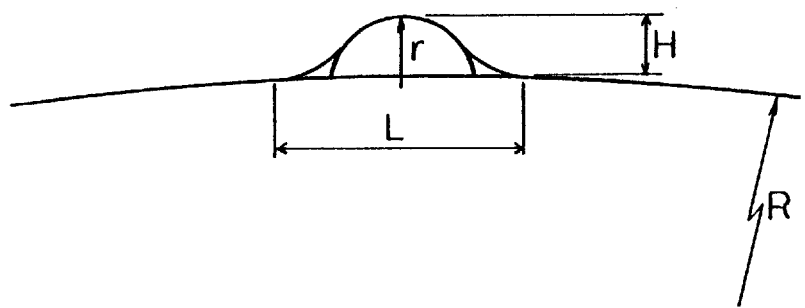
FIG. 13 is a diagram illustrative of parameters for defining the depth or degree of a surface distortion.

A decision as to whether the surface distortion is acceptable or not is finally made using the range L and degree H of distortion, and curvature data r, R at the central point $x_P$ in a step S20. FIG. 13 schematically shows the relationship between the range L and degree or depth H of distortion, and curvature data r, R.

Figure 14A:
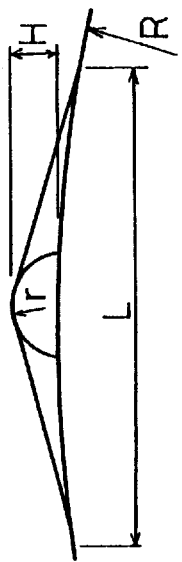
FIGS. 14A through 14D are diagram illustrative of surface distortions in respective modes which are defined by the parameters shown in FIG. 13.
Figure 14B:
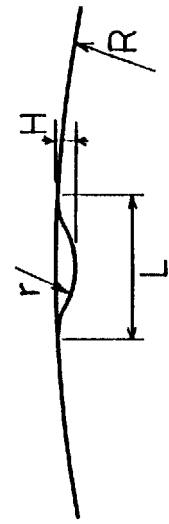
Figure 14C:
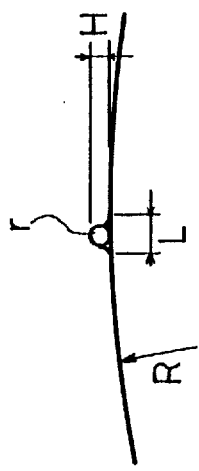
Figure 14D:
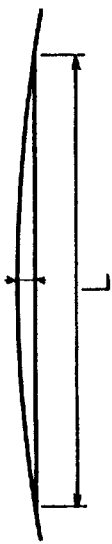

As shown in FIG. 14A, when H>0 and r≈H≈L, the surface distortion is noticeable even if the degree H of distortion is small. As shown in FIG. 14B, when H>0, r<<H<<L, the surface distortion is less noticeable even if the degree H of distortion is large, but becomes more noticeable if the curvature data r is smaller. As shown in FIG. 14C, when H<0 and r≈R≈∞, the surface distortion is less noticeable even if the degree H of distortion is large. As shown in FIG. 14D, when H<0, the surface distortion may be noticeable depending on the magnitude of the curvature data R even if the degree H of distortion is small.

Figure 15:
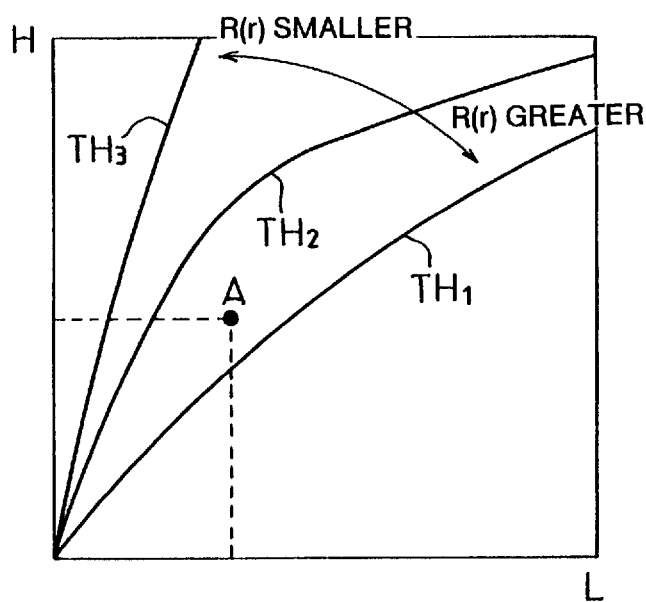
FIG. 15 is a diagram showing the relationship between decision reference data and the parameters shown in FIG. 13.

In view of the surface distortions in the respective modes shown in FIGS. 14A through 14D, decision reference data $TH_1 \sim TH_3$ are established, as shown in FIG. 15, such that their gradient is greater as the curvature data r or R is greater. The profile evaluating device 104 selects one of the decision reference data $TH_1 \sim TH_3$ shown in FIG. 15 which corresponds to the curvature data r of the smoothed data $s_i$ representing the cross section of the surface of the vehicle body 16 and the curvature data R in the approximate equation f(x) corresponding to the surface distortion. Then, it is determined in FIG. 15 on which side of the boundary of the selected decision reference data a point A is positioned which corresponds to the degree H and range L of distortion on the vehicle body 16, and it is then determined whether the surface distortion is acceptable or not based on the determined side. For example, when the selected decision reference data is $TH_1$, if the point A is positioned higher than the decision reference data $TH_1$, then the surface distortion is judged as large, and if the point A is positioned lower than the decision reference data $TH_1$, then the surface distortion is judged as small.

In the above embodiment, the cubic approximate equation f(x) of the smoothed data $s_i$ is used as representing the reference surface profile data for the vehicle body. However, surface profile data produced at the time the vehicle body is designed and supplied from the CAD device 106 may be used.

Figure 16:
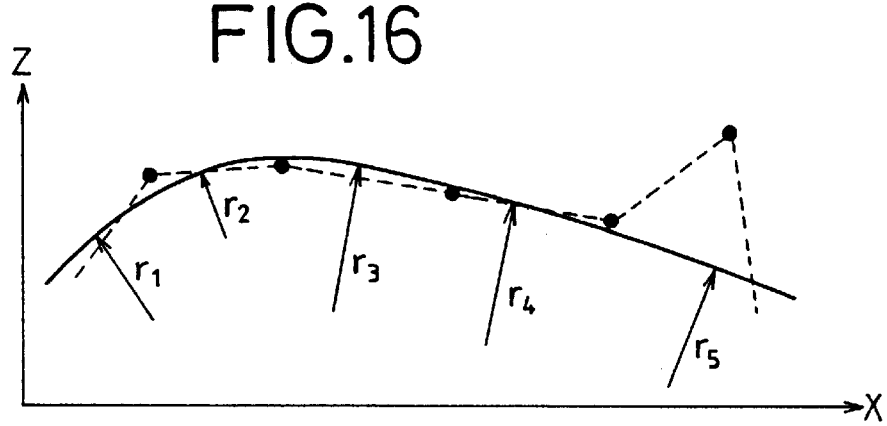
FIG. 16 is a diagram illustrative of a process of smoothing measured surface profile data.
Figure 17:
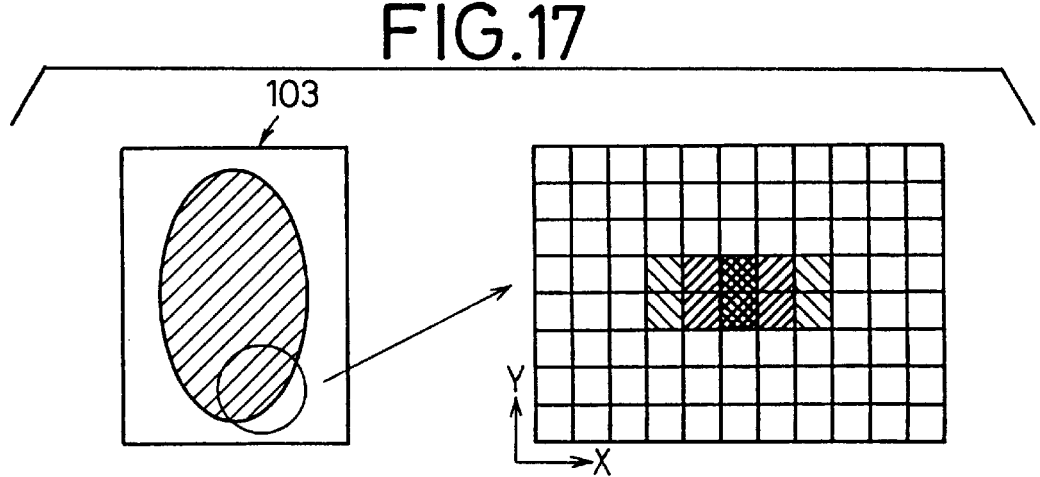
FIG. 17 is a view showing an image displayed on a CRT display in the surface inspecting method.

A surface inspecting process may be carried out by the profile evaluating device 104 as follows:

After the surface profile of the vehicle body 16 is measured and smoothed data $s_i$ is generated as shown in FIG. 16, the profile evaluating device 104 reads the reference surface profile data of the vehicle body 16 from the CAD device 106, and calculates deviation data H thereof in the direction of the Z-axis from the measured surface profile data at the distances ΔX, ΔY. The deviation data H is divided by a given distance δh, thus calculating stepwise deviation data [H/δh] where [ ] represents a Gauss' symbol for rounding off the value of H/δh into an integer. Respective colors are established with respect to the stepwise deviation data [H/δh], and the deviation data [H/δh] of the vehicle body 16 whose various areas are colored by the colors are displayed in corresponding patterns thereof on the display monitor 103 (see FIG. 17).

Figure 18:
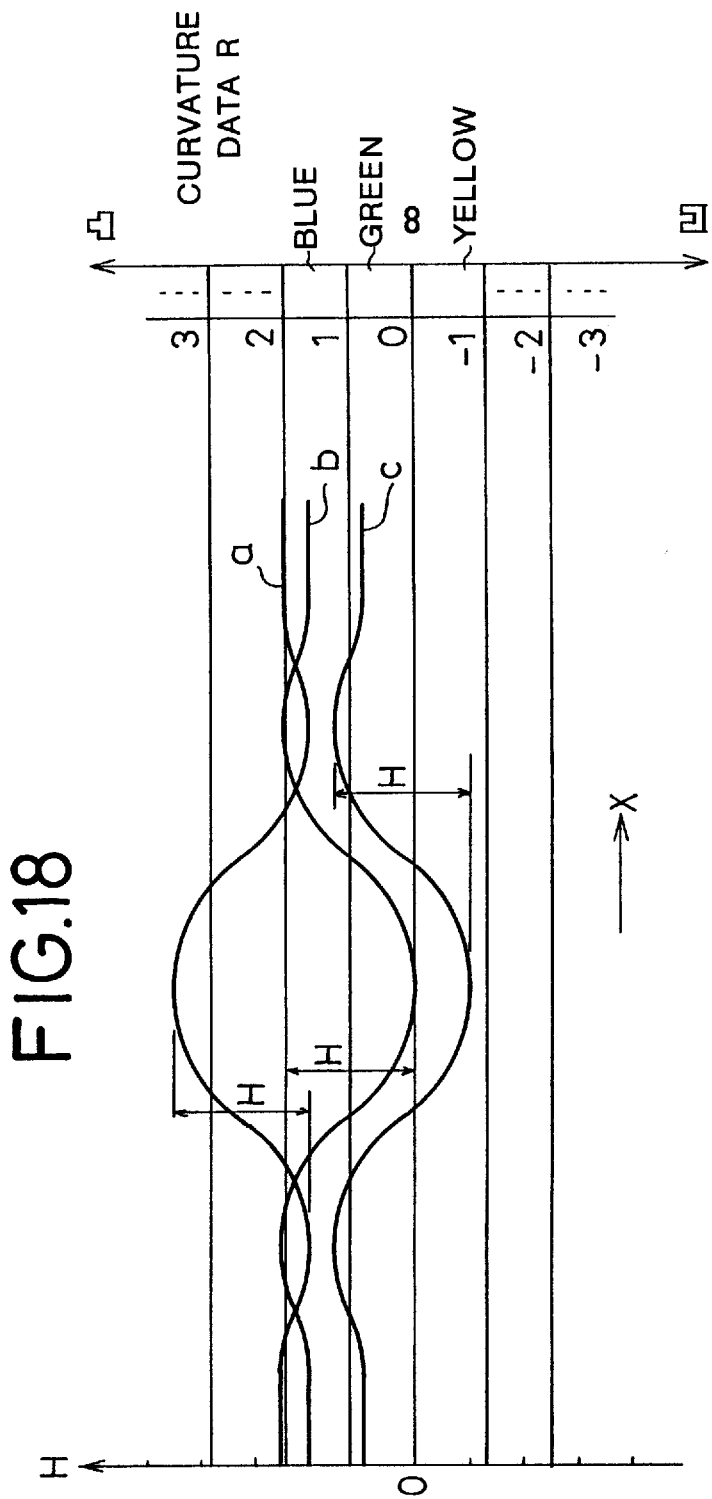
FIG. 18 is a diagram showing the relationship between deviation data and stepwise deviation data in the surface inspecting method.

FIG. 18 shows the relationship between the deviation data H in respective positions on the vehicle body 16 in the direction of the X-axis and the stepwise deviation data [H/δh]. In FIG. 18, respective colors are established with respect to the stepwise deviation data [H/δh]=−3, −2, −1, 0, 1, 2, 3. If the difference ΔH between maximum and minimum values of the deviation data H on each of characteristic curves a, b, c extends four or more steps in terms of the stepwise deviation data [H/δh], then since four or more colors are displayed on the display monitor 103, the surface profile of the vehicle body 16 is judged as being defective.

A surface inspecting method according to still another embodiment of the present invention will be described below.

Figure 19:
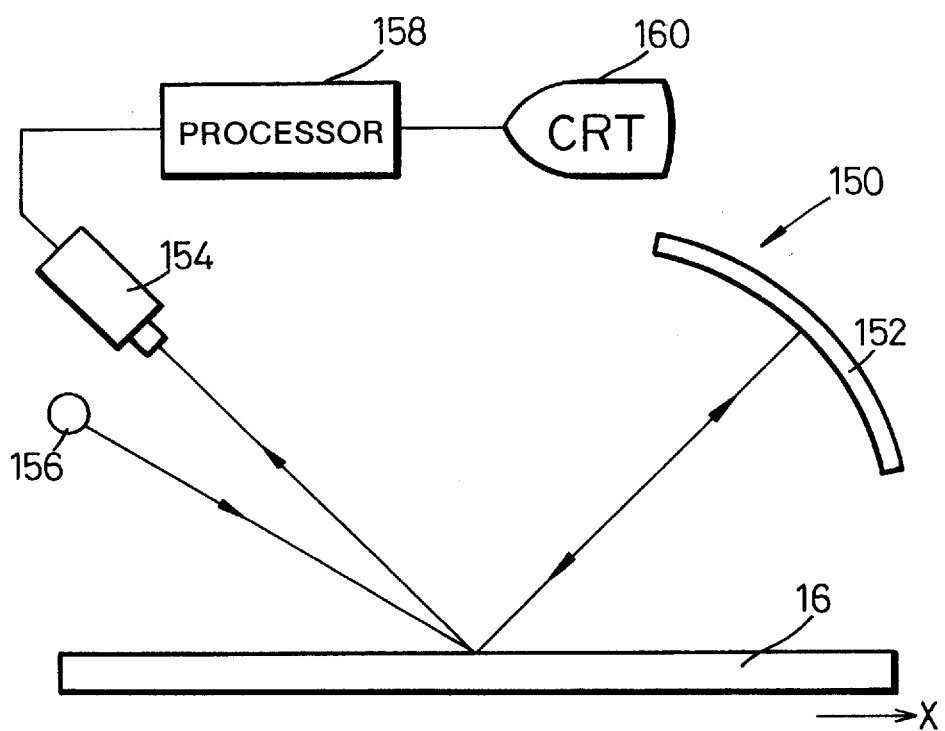
FIG. 19 is a schematic view illustrative of still another surface inspecting apparatus.

FIG. 19 schematically shows still another surface inspecting apparatus. The surface inspecting apparatus, generally denoted at 150, has a light reversing screen 152, a camera 154, and a light source 156 as essential elements. Illuminating light emitted from the light source 156 is reflected by the surface of the vehicle body 16 toward the light reversing screen 152, which reflects the light again. The reflected light is then applied via the vehicle body 16 to the camera 154. The camera 154 captures an image which represents optically emphasized surface irregularities of the vehicle body 16.

To the camera 154, there is connected a processor 158 which processes luminance information obtained from the image to determine a range L and degree H of distortion (see FIG. 13) which constitute reference data for determining whether a surface distortion of the vehicle body 16 is acceptable or not. The processor 158 is connected to a display monitor 160 such as a CRT or the like for displaying the image read by the camera 154 and other information.

Figure 20:
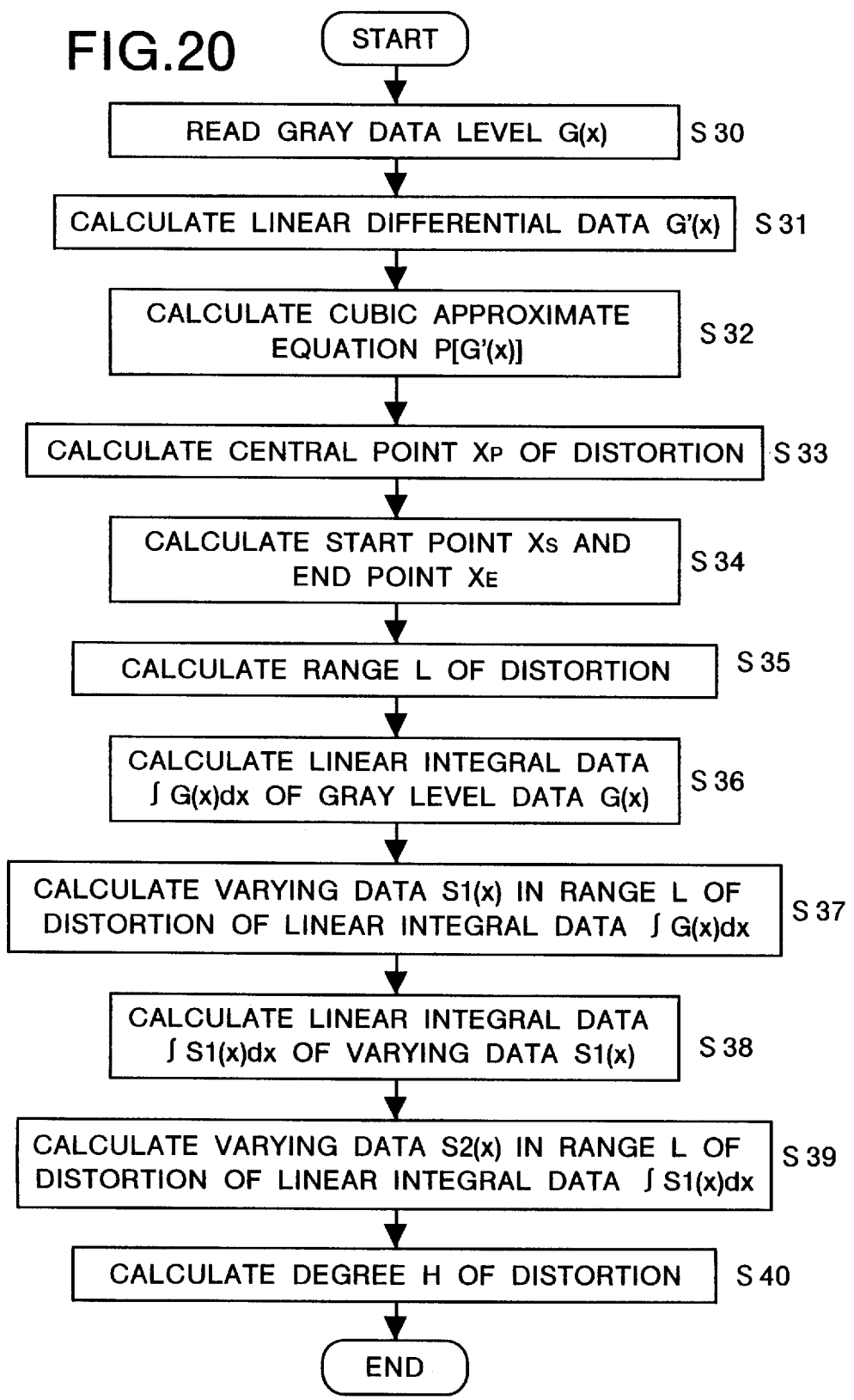
FIG. 20 is a flowchart of an operation sequence of a surface inspecting method according to still another embodiment of the present invention.

A process of determining the range L and degree H of distortion will be described below with reference to FIG. 20.

Figure 21:
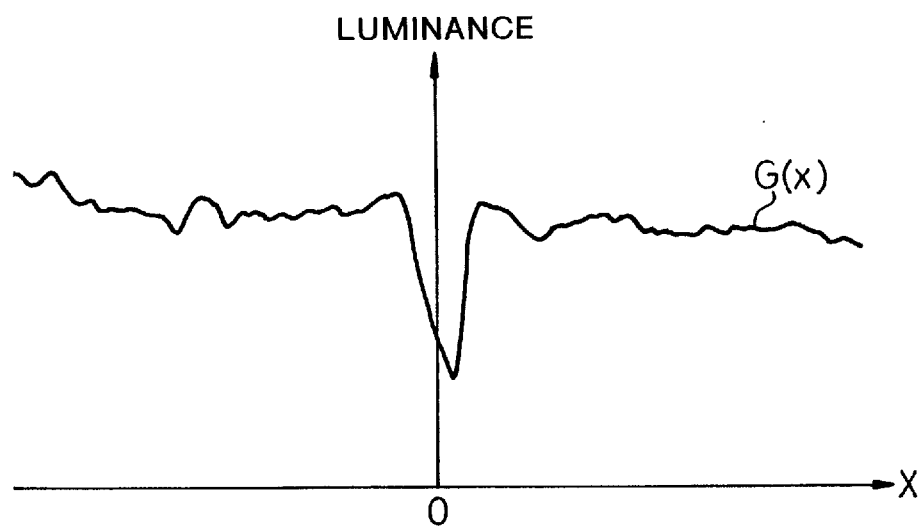
FIG. 21 is a diagram of gray level data which represents luminance information of the surface of a vehicle body which is obtained by the surface inspecting apparatus shown in FIG. 19.

First, luminance information on a line along the direction of the X-axis shown in FIG. 19 is extracted as gray level data $G(x)$ from the luminance information of the vehicle body 16 which has been read by the camera 154, in a step S30. FIG. 21 shows the gray level data $G(x)$ at a coordinate x of the vehicle body 16. In FIG. 21, the surface of the vehicle body 16 has a convex distortion whose luminance is lower than the luminance of other areas.

Figure 22:
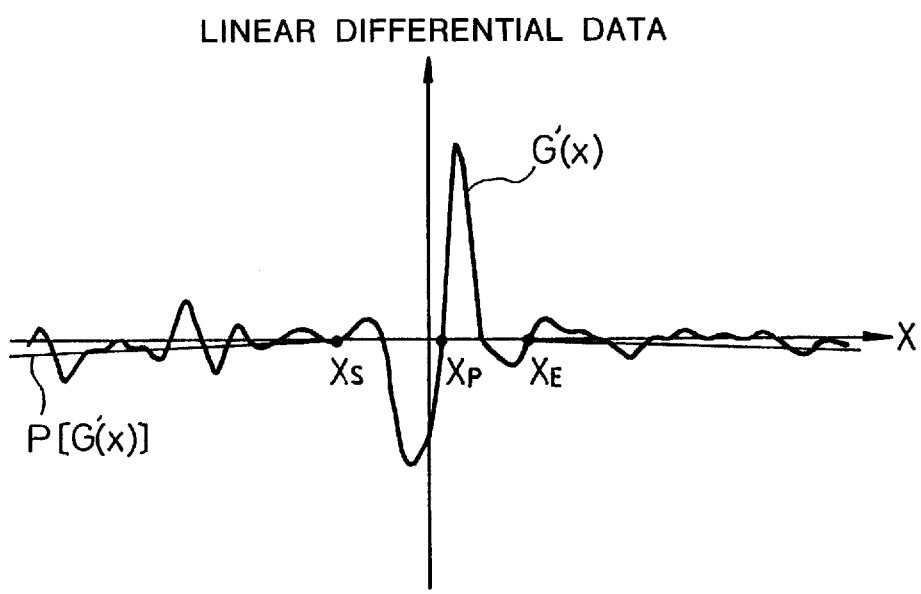
FIG. 22 is a diagram of linear differential data produced when the gray level data shown in FIG. 21 is differentiated and a cubic approximate equation of such linear differential data.

Then, the gray level data $G(x)$ is differentiated into linear differential data $G'(x)$ in a step S31. A cubic approximate equation $P[G'(x)]$ of the linear differential data $G'(x)$ is determined using the method of least squares in a step S32. FIG. 22 shows the linear differential data $G'(x)$ and the cubic approximate equation $P[G'(x)]$ thereof as they overlap each other. Because the cubic approximate equation $P[G'(x)]$ represents a smoothed form of the linear differential data $G'(x)$, it is regarded as linear differential data produced from the surface of the vehicle body in which no distortions are visually recognized. The difference between the linear differential data $G'(x)$ and the cubic approximate equation $P[G'(x)]$ thereof represents the extent of a distortion that can be visually recognized.

An X-axis coordinate where the linear differential data $G'(x)$ at its maximum amplitude intersects with the cubic approximate equation $P[G'(x)]$ is established as a central point $x_P$ of the distortion in a step S33. If the distortion of the vehicle body 16 is small, then since the cubic approximate equation $P[G'(x)]$ is substantially aligned with the X-axis, an X-axis coordinate where the linear differential data $G'(x)$ at its maximum amplitude intersects with the X-axis may be established as a central point $x_P$ of the distortion.

Figure 23:
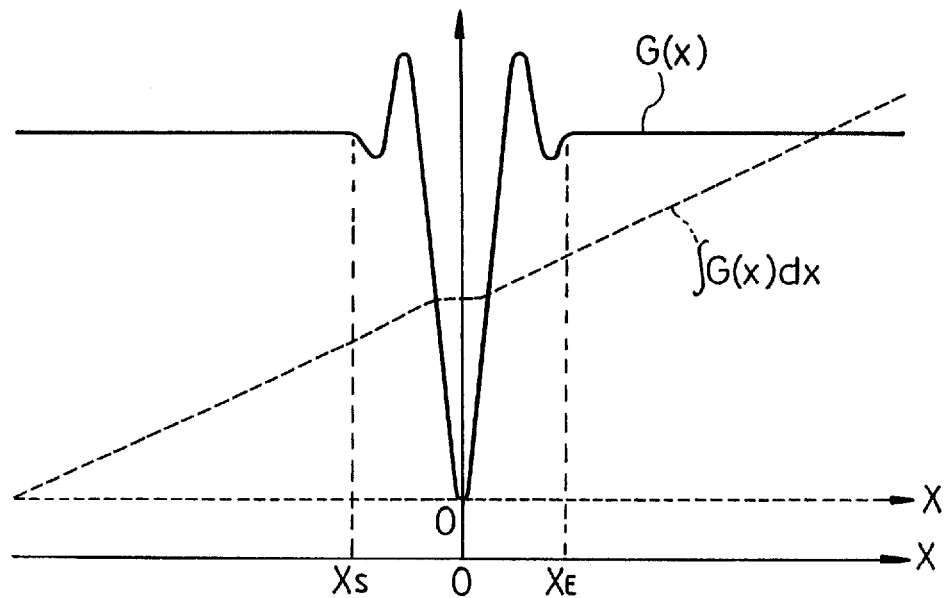
FIG. 23 is a diagram of linear integral data produced when the gray level data shown in FIG. 21 is successively integrated.

Then, a start point $x_S$ and an end point $x_E$ of the distortion, positioned one on each side of the central point $x_P$, are determined in a step S34. If the vehicle body 16 has the distortion shown in FIG. 13 and the luminance information obtained from the distortion is emphasized or sharpened in edge, the gray level data $G(x)$ is produced as shown in FIG. 23. If the X-axis coordinates of minimum values positioned one on each side of the central point $x_P$ of the distortion of the gray level data $G(x)$ are defined respectively as a start point $x_S$ and an end point $x_E$ of the distortion, these points can be determined as the coordinates of points, positioned one on each side of the central point $x_P$, of the linear differential data $G'(x)$ which become nil the second time, as shown in FIG. 22.

The range L of distortion is determined from the coordinates of the start point $x_S$ and the end point $x_E$ thus calculated in a step S35. The range L of distortion can be calculated by transforming the coordinates of the start point $x_S$ and the end point $x_E$ as follows:

$$L = \alpha \cdot |x_S - x_E| \quad (5)$$

where $\alpha$ is a coefficient established in view of the angle at which the camera 154 is inclined with respect to the vehicle body 16 and the magnification ratio at which the image is read. The range L of distortion thus determined is not affected by rounding errors produced upon conversion into binary values, and can be determined highly accurately depending on the accuracy of the linear differential data $G'(x)$.

The degree H of distortion can be determined highly accurately by integrating the gray level data $G(x)$ twice. Specifically, if the cross-sectional shape of the vehicle body 16 is of a sinusoidal wave, then its quadratic differential waveform comprises a sinusoidal wave which is 180° out of phase with the sinusoidal cross-sectional shape. The relationship between these two sinusoidal waves is analogous to the relationship between the gray level data $G(x)$ composed of luminance information and the cross-sectional shape data of the vehicle body 16. Therefore, it is presumed that data analogous to the cross-sectional shape of the vehicle body 16 is obtained when the gray level data $G(x)$ is inversely integrated twice.

First, the gray level data $G(x)$ at respective coordinates x are successively integrated into linear integral data $\int G(x)dx$ in a step S36. The linear integral data $\int G(x)dx$ is plotted as a dotted-line curve with respect to the gray level data $G(x)$ in FIG. 23.

Figure 24:
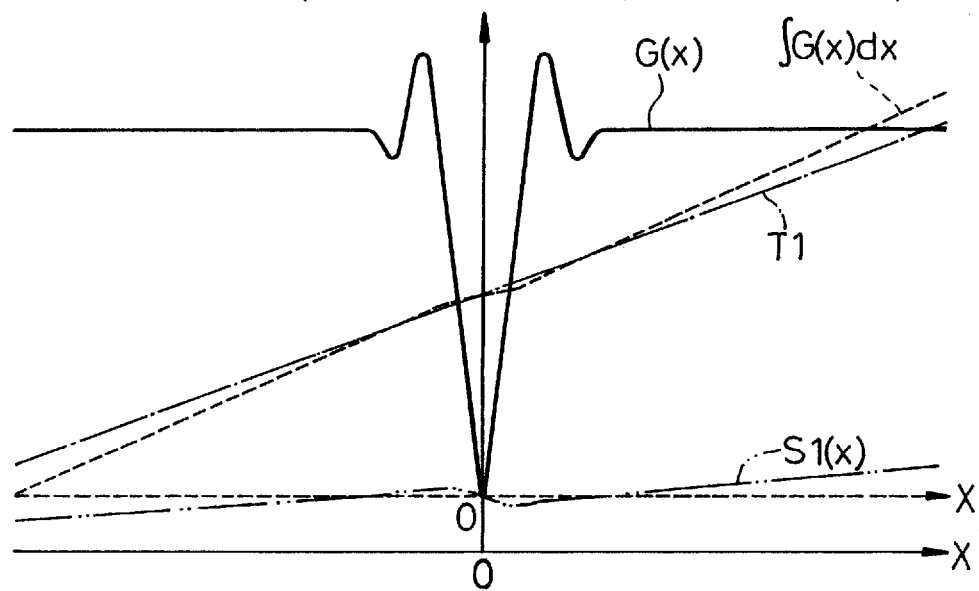
FIG. 24 is a diagram of varying data produced from the linear integral data shown in FIG. 23.
Figure 25:
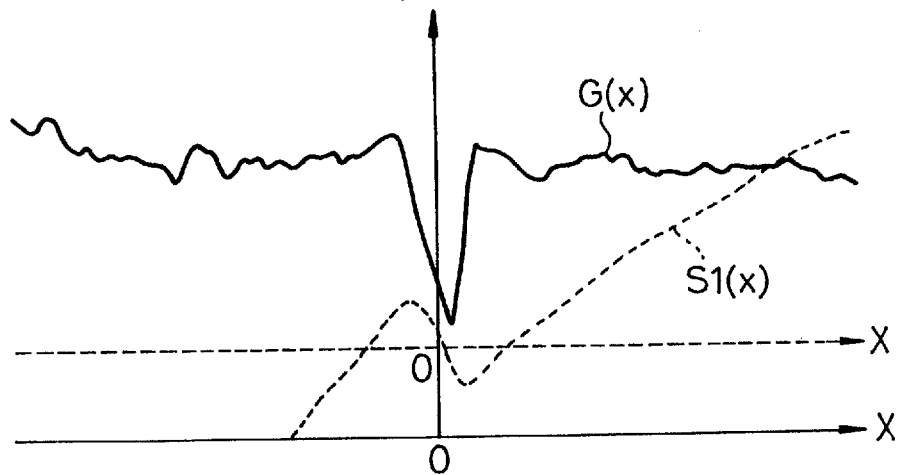
FIG. 25 is a diagram of linear integral data produced from the gray level data shown in FIG. 21.

A straight line T1 that passes through the start point $x_S$ and the end point $x_E$ is determined with respect to the linear integral data $\int G(x)dx$, and the difference between the straight line T1 and the linear integral data $\int G(x)dx$ is determined as varying data $S1(x)$ in the range L of distortion in a step S37 (see FIG. 24). The varying data $S1(x)$ is nil if the vehicle body 16 is free of surface distortions. Therefore, data relative to the degree of distortion of the vehicle body 16 can be extracted by determining the varying data $S1(x)$. With respect to the gray level data $G(x)$ shown in FIG. 21, varying data $S1(x)$ shown in FIG. 25 is obtained.

Figure 26:
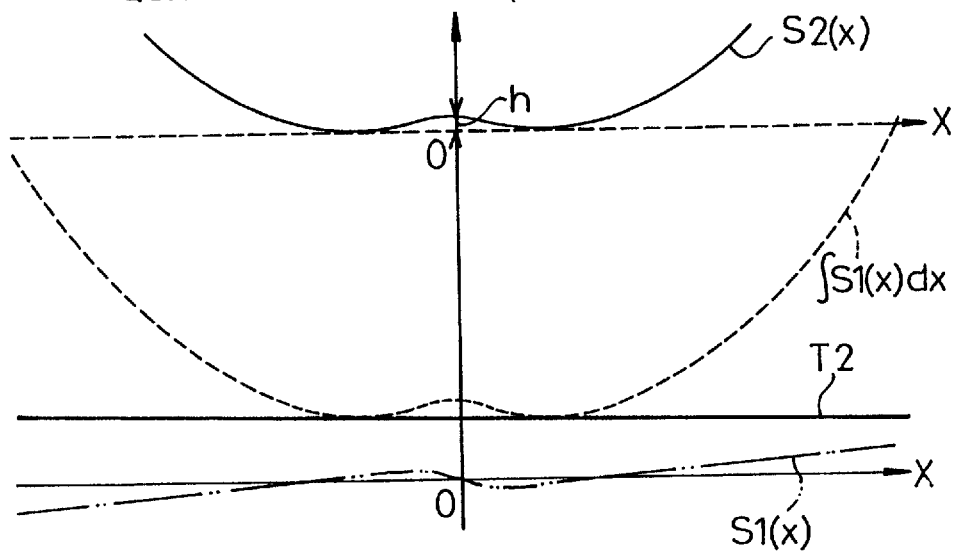
FIG. 26 is a diagram of varying data produced from quadratic integral data generated from the gray level data shown in FIG. 21.
Figure 27:
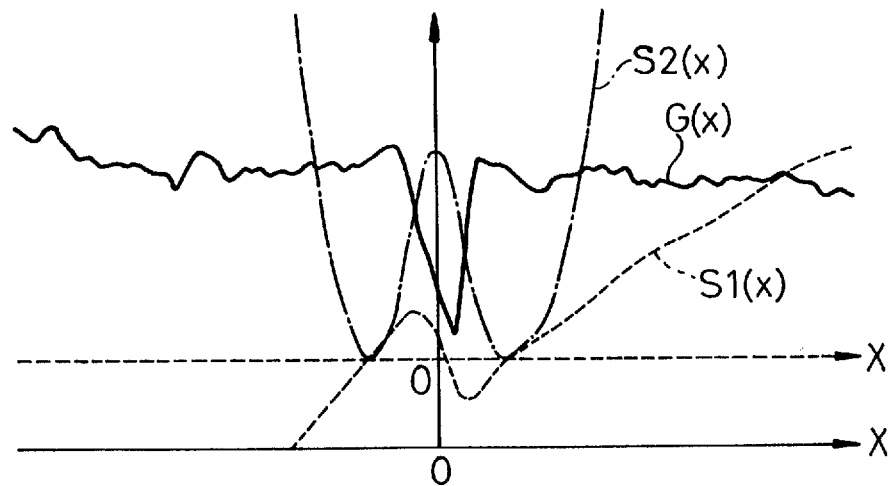
FIG. 27 is a diagram of linear and quadratic integral data produced from the gray level data shown in FIG. 21.

Similarly, linear integral data $\int S1(x)dx$ is determined from the varying data $S1(x)$ in a step S38. Then, a straight line T2 that passes through the start point $x_S$ and the end point $x_E$ is determined with respect to the linear integral data $\int S1(x)dx$ (see FIG. 26), and the difference between the straight line T2 and the linear integral data $\int S1(x)dx$ is determined as varying data $S2(x)$ in the range L of distortion in a step S39. With respect to the gray level data $G(x)$ shown in FIG. 21, varying data $S2(x)$ shown in FIG. 27 is obtained.

Figure 28:
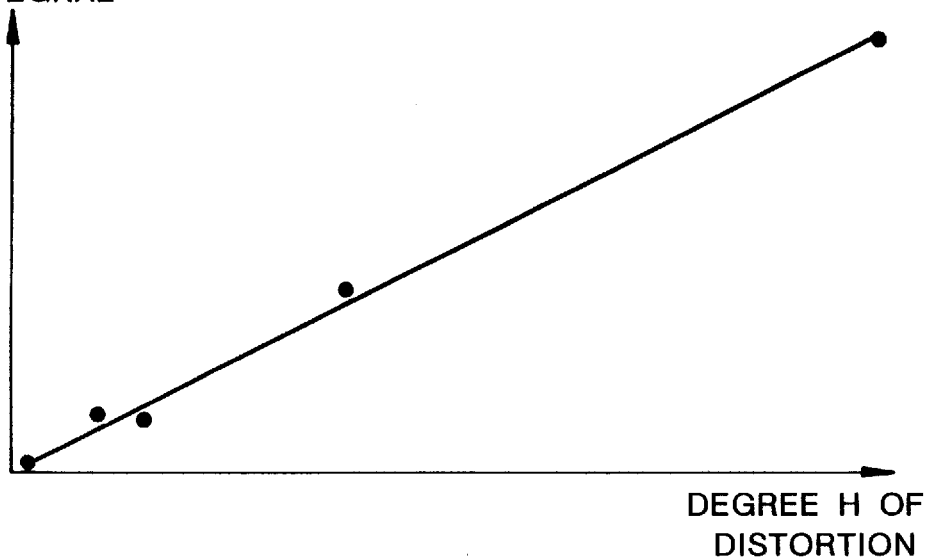
FIG. 28 is a diagram illustrative of the relationship between the quadratic integral data and the degree of distortion.

It has been confirmed that there is a good linear relationship, as shown in FIG. 28, between the maximum value h between the start point $x_S$ and the end point $x_E$ of the varying data $S2(x)$ thus determined and an actually measured degree H of distortion. The degree H of distortion is determined in a step S40 by:

$$H = \beta \cdot h \quad (6)$$

where $\beta$ is a coefficient derived from the linear relationship shown in FIG. 28.

It can be determined whether the surface distortion of the vehicle body 16 is acceptable or not in the same manner as described above with reference to FIGS. 13 through 15, using the range L and degree H of distortion thus determined as reference data.

According to the present invention, as described above, after outer panels have been assembled on a vehicle frame and immediately before they are coated, the outer panels are inspected for surface distortions and repaired, if necessary. Therefore, the yield of products, e.g., vehicle bodies, is increased after they are coated, and the efficiency of manufacturing and inspecting operation is increased.

A lustering agent that is coated on the surface of a vehicle body before it is inspected for surface distortions can be handled with ease because it comprises an aqueous lustering agent. Inasmuch as the aqueous lustering agent is used, a thin lustrous film of sufficiently uniform thickness can be formed on the surface of the vehicle body even if the lustering agent is applied under pneumatic pressure. Consequently, an appropriate surface treatment is given to the vehicle body inexpensively.

A point where linear differential data of measured surface profile data, produced by measuring the surface profile of a product or vehicle body, and smoothed linear differential data, produced by smoothing the linear differential data, intersect with each other is regarded as a central point of a distortion. The degree of distortion at the central point is determined, and quadratic differential data is calculated from the linear differential data. A range of distortion is determined from a range in which the quadratic differential data varies greatly. These determined values are used to determine appropriately whether the distortion is acceptable or not.

It can be determined more appropriately whether the distortion is acceptable or not, using the curvature at the central point of the distortion in addition to the degree and range of distortion.

The degree and range of distortion which serve as reference data for determining a surface distortion can be calculated highly accurately from luminance information of the surface of the vehicle body. Therefore, it can be determined highly accurately whether the surface of the vehicle body is acceptable or not, using the reference data.

Deviations between measured surface profile data and reference surface profile data are displayed in different colors in steps corresponding to the magnitudes of the deviations. Consequently, the extent of a surface distortion can clearly be recognized, making it possible to determine easily whether the surface distortion is acceptable or not.

Furthermore, according to the present invention, a decision reference for a surface distortion is established based on a reference surface profile in a range in which deviations occur, and a surface distortion is determined according to the decision reference. As a result, only a surface distortion which is visually noticeable can automatically be extracted without relying on a subjective decision.

Although certain preferred embodiments of the present invention have been shown and described in detail, it should be understood that various changes and modifications may be made therein without departing from the scope of the appended claims.

What is claimed is:

1. A method of manufacturing a vehicle body, comprising:
   assembling outer panels on a vehicle frame, producing a vehicle body;
   coating an aqueous lustering agent diluted to a predetermined concentration to a surface of said vehicle body under pneumatic pressure with a spray means, thereby forming a thin lustrous film on the surface of the vehicle body;
   measuring a degree of surface distortion of the surface of the vehicle body, including the outer panels;
   identifying a defective area of the surface by comparing said degree of surface distortion with a predetermined decision value, thereby determining whether said surface distortion is acceptable or not;
   if the defective area is not acceptable, repairing said defective area; and
   delivering the vehicle body with the defective area repaired to a coating station,
   wherein said aqueous lustering agent comprises one of an anionic surface-active agent diluted to said predetermined concentration by water and an emulsion of a cationic or aqueous surface-active agent and a petroleum solvent.

2. A method according to claim 1, wherein said step of determining comprises the steps of:
   applying a light beam to the surface of the vehicle body; and
   processing light reflected by the surface of the vehicle body.

3. A method of inspecting a vehicle body, comprising the steps of:
   measuring a surface profile of a vehicle body, producing measured surface profile data;
   differentiating said measured surface profile data into linear differential data;
   smoothing said linear differential data into smoothed linear differential data;
   determining a central point of a distortion from said smoothed linear differential data and said linear differential data;
   determining the difference between reference surface profile data of the vehicle body and said measured surface profile data at said central point, as a degree of distortion;
   differentiating said linear differential data into quadratic differential data;
   determining a range of distortion around said central point from said quadratic differential data; and
   determining whether the distortion of the vehicle body is acceptable or not based on said degree of distortion and said range of distortion.

4. A method according to claim 3, further comprising the steps of:
   after said step of determining a range of distortion, determining a curvature at said central point from said reference surface profile data and a curvature at said central point from said measured surface profile data; and
   determining whether the distortion of the vehicle body is acceptable or not based on said degree of distortion, said range of distortion, and the distortions.

5. A method according to claim 4, wherein said step of determining whether the distortion of the vehicle body is acceptable or not comprises the step of:
   determining whether the distortion of the vehicle body is acceptable or not based on said degree of distortion and said range of distortion with respect to decision reference data which is established such that the gradient thereof is greater as each of the curvatures is greater.

6. A method according to claim 3, wherein said step of measuring comprises the steps of:
   applying a light beam to the surface of the vehicle body; and
   processing light reflected by the surface of the vehicle body.

7. A method according to claim 3, wherein said step of determining a central point comprises the step of:

determining the central point as a point where said linear differential data changes from a value greater than said smoothed linear differential data to a value smaller than said smoothed linear differential data, or from a value smaller than said smoothed linear differential data to a value greater than said smoothed linear differential data.

8. A method according to claim 3, wherein said step of determining a range of distortion comprises the step of:

extracting a maximum value of said quadratic differential data which is greater or smaller than a predetermined value.

9. A method according to claim 3, further comprising the step of:

smoothing said measured surface profile data into smoothed measured surface profile data as said reference surface profile data.

10. A method according to claim 3, wherein said step of smoothing said linear differential data comprises the step of:

processing said linear differential data according to the method of least squares.

11. A method of inspecting a vehicle body, comprising the steps of:

obtaining luminance data depending on a surface profile of a vehicle body from light reflected by a surface of the vehicle body irradiated with illuminating light;

differentiating said luminance data into linear differential data;

determining a central point of a distortion of the surface profile from said linear differential data;

determining a range of distortion around said central point from said linear differential data;

integrating said luminance data twice in said range of distortion, determining quadratic integral data; and determining a degree of distortion of said surface profile from said quadratic integral data.

12. A method according to claim 11, wherein said step of determining a central point comprises the step of:

determining the central point as a position in which said linear differential data at its maximum amplitude intersects with smoothed linear differential data which is produced by smoothing said linear differential data.

13. A method according to claim 11, wherein said step of determining a range of distortion comprises the step of:

determining the range of distortion as a distance between two points where said linear differential data becomes nil the second time in each of positive and negative directions from a reference position at the central point of the distortion of said linear differential data.

14. A method according to claim 11, wherein said step of determining a degree of distortion comprises the step of:

determining the degree of distortion from a maximum value of said quadratic integral value in said range of distortion;

measuring a surface profile of a vehicle body, producing measured surface profile data.

15. A method of inspecting a vehicle body, comprising the steps of:

measuring a surface profile of a vehicle body, producing measured surface profile data;

determining deviation data between reference surface profile data of the vehicle body and said measured surface profile data at a predetermined pitch on the surface profile corresponding to a given location of the vehicle body;

converting said deviation data into stepwise deviation data in a plurality of ranks;

displaying said stepwise deviation data depending on the surface profile of the vehicle body, in different colors established with respect to the ranks, each of said displayed ranks corresponding to a different location of the vehicle body, respectively; and determining a surface distortion of the vehicle body, at said given location based on the stepwise deviation data displayed in said different colors.

16. A method according to claim 15, wherein said step of measuring comprises the steps of:

applying a light beam to the surface of the vehicle body; and processing light reflected by the surface of the vehicle body.

17. A method according to claim 15, wherein said step of measuring comprises the steps of:

applying a light beam to the surface of the vehicle body; and processing light reflected by the surface of the vehicle body.

18. A method of inspecting a vehicle body, comprising the steps of:

measuring a surface profile of a vehicle body, producing measured surface profile data;

determining deviation data between reference surface profile data of the vehicle body and said measured surface profile data at a predetermined pitch on the surface profile;

establishing decision reference data based on at least a profile composed of said reference surface profile data in a range in which said deviation data is not nil, wherein a gradient of said decision reference data is greater as respective curvatures of said reference surface profile data and said measured surface profile data are greater in said range; and comparing said decision reference data and the deviation data in said range thereby to determine a surface distortion of the vehicle body.

19. A method of manufacturing a vehicle body, comprising:

assembling outer panels on a vehicle frame, producing a vehicle body;

coating an aqueous lustering agent diluted to a predetermined concentration ranging from 15 to 20% to a surface of said vehicle body under pneumatic pressure with a spray means, thereby forming a thin lustrous film on the surface of the vehicle body;

measuring a degree of surface distortion of the surface of the vehicle body, including the outer panels;

identifying a defective area of the surface by comparing said degree of surface distortion with a predetermined decision value, thereby determining whether said surface distortion is acceptable or not;

if the defective area is not acceptable, repairing said defective area; and delivering the vehicle body with the defective area repaired to a coating station.

20. A method according to claim 19, wherein said step of determining comprises the steps of:

applying a light beam to the surface of the vehicle body; and processing light reflected by the surface of the vehicle body.

21. A method according to claim 19, wherein said aqueous lustering agent comprises an anionic surface-active agent diluted to said predetermined concentration by water.

22. A method according to claim 19, wherein said aqueous lustering agent comprises an emulsion of a cationic or aqueous surface-active agent and a petroleum solvent.

* * * * *